US008628760B2

(12) United States Patent
Carter et al.

(10) Patent No.: US 8,628,760 B2
(45) Date of Patent: Jan. 14, 2014

(54) PERSONAL CARE COMPOSITION COMPRISING A NEAR-TERMINAL BRANCHED COMPOUND

(75) Inventors: John David Carter, Mason, OH (US); Elaine Marie Burt, Cincinnati, OH (US); Jeffrey John Scheibel, Loveland, OH (US); David Johnathan Kitko, Cincinnati, OH (US); Jun Xu, Mason, OH (US); Charles Winston Saunders, Fairfield, OH (US); Kenneth Nathan Price, Cincinnati, OH (US); Stephanie Ann Urbin, Cincinnati, OH (US); Phillip Richard Green, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 219 days.

(21) Appl. No.: 13/182,943

(22) Filed: Jul. 14, 2011

(65) Prior Publication Data
US 2012/0014900 A1    Jan. 19, 2012

Related U.S. Application Data

(60) Provisional application No. 61/364,519, filed on Jul. 15, 2010.

(51) Int. Cl.
*A61Q 5/12* (2006.01)
*A61K 47/00* (2006.01)

(52) U.S. Cl.
USPC ........................... 424/70.12; 514/785

(58) Field of Classification Search
USPC ...................... 424/70.122; 514/785
See application file for complete search history.

(56) References Cited

U.S. PATENT DOCUMENTS

| 6,335,312 | B1* | 1/2002 | Coffindaffer et al. | 510/159 |
| 6,531,143 | B1* | 3/2003 | Yakumaru et al. | 424/401 |
| 8,147,813 | B2 | 4/2012 | Beauquey et al. | |
| 2004/0076654 | A1 | 4/2004 | Vinson et al. | |
| 2009/0221463 | A1 | 9/2009 | Kitko et al. | |
| 2012/0012130 | A1 | 1/2012 | Hutton, III et al. | |
| 2012/0014900 | A1 | 1/2012 | Carter et al. | |
| 2012/0014901 | A1 | 1/2012 | Sunkel et al. | |

FOREIGN PATENT DOCUMENTS

JP   2000-344697   12/2000

OTHER PUBLICATIONS

U.S. Appl. No. 13/182,990, filed Jul. 14, 2011, Scheibel.

* cited by examiner

*Primary Examiner* — Blessing M Fubara
*Assistant Examiner* — Jennifer Berrios
(74) *Attorney, Agent, or Firm* — Angela K. Haughey

(57) ABSTRACT

A personal care composition comprising: a near-terminal branched compound according to Formula I; a cosmetically acceptable aqueous carrier; wherein the near-terminal branched compound is not comprised in a gel network.

14 Claims, No Drawings

PERSONAL CARE COMPOSITION COMPRISING A NEAR-TERMINAL BRANCHED COMPOUND

CROSS REFERENCE TO RELATED APPLICATION

This application claims the benefit of U.S. Provisional Application No. 61/364,519, filed Jul. 15, 2010.

FIELD OF THE INVENTION

A personal care composition comprising: a near-terminal branched compound according to Formula I; a cosmetically acceptable aqueous carrier; wherein the near-terminal branched compound is not comprised in a gel network.

BACKGROUND OF THE INVENTION

Human hair becomes dry and/or damaged due to the surrounding environment, styling, regular cleansing, drying, and/or coloring or otherwise chemically treating the hair.

A variety of approaches have been developed to condition the hair. A common method of providing conditioning benefit is through the use of hair care compositions containing conditioning agents such as cationic surfactants and polymers, high melting point fatty compounds, low melting point oils, silicone compounds, and mixtures thereof. Silicones are often used as a conditioning active for a number of hair care compositions. However, the rising costs, demand for better conditioning of damaged hair, and the petroleum-based nature of silicone has minimized its desirability as a conditioning active. Moreover, high levels of conventional silicones can often cause consumer-perceived tradeoffs in clean feel e.g. stickiness, coated feel.

Based on the foregoing, there is a need for a conditioning active which can provide conditioning benefits to hair which can replace, or be used in combination with silicone, or other conditioning active, to maximize the conditioning activity of a hair care composition. Additionally, there is a need to find a conditioning active which can deliver an improved conditioning benefit to damaged hair, which has previously been difficult to condition using traditional conditioning actives. There is also a need to find a conditioning active which can be derived from a natural and renewable resource. There are environmental concerns around the expanding use of silicones in personal care products and also increasing concerns in relation to their biodegradation. Furthermore, there is a need for producing conditioning actives via less energy intensive processes.

There has been an increase in the number of hair care products with 'silicone free' claims on the market. However, there remains a need for conditioning formulations with an improved sustainability profile in combination with conditioning benefits near-parity to traditional silicone conditioning formulations. More specifically there is a constant need for more sustainable conditioning formulations with excellent wet and dry conditioning efficacy across a range of hair types.

SUMMARY OF THE INVENTION

According to a first aspect, the present invention relates to a personal care composition comprising:
(a) a near-terminal branched compound according to Formula I

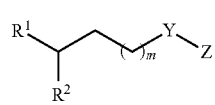

wherein $R^1$ is methyl, ethyl or propyl; $R^2$ is methyl, ethyl or propyl; m is alkyl or alkenyl comprising a carbon chain of 5 to 19 carbons; Y is null or $W_p$; W is selected from the group consisting of ethylenoxy, propylenoxy, butylenoxy, and mixtures thereof; p is 1 to 30; Z is a monovalent substituent selected from the group consisting of:
—O(C=O)$R^3$, —COO$R^3$, —N$R^3$(C=O)$R^3$, —NH(C=O)$R^3$, —NCH$_3$(C=O)$R^3$, —CONH$R^3$, —CON($R^3$)$_2$, —O$R^3$, —OCH$_2$CH(O$R^3$)CH$_2$O$R^3$ and —OP=O(OH)O$R^3$, wherein $R^3$ is either:
i) a linear alkyl or alkenyl comprising a carbon chain of 8 to 24 carbons, or
ii) a near-terminal branched alkyl chain according to Formula II

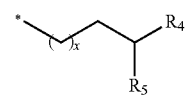

wherein $R^4$ is methyl, ethyl or propyl; $R^5$ is methyl, ethyl or propyl;
x is alkyl or alkenyl comprising a carbon chain of 5 to 19 carbons;
(b) a cosmetically acceptable aqueous carrier;
wherein the near-terminal branched compound is not comprised in a gel network.

According to a second aspect, the present invention relates to a conditioning shampoo formulation for cleansing hair comprising:
(a) a near-terminal branched compound as defined in the first aspect;
(b) a cosmetically acceptable aqueous carrier;
(c) a cationic polymer;
(d) anionic surfactant;
wherein the near-terminal branched compound is not comprised in a gel network.

According to a third aspect, the present invention relates to a rinse-off conditioner formulation comprising:
(a) a near-terminal branched compound as defined in the first aspect;
(b) a cosmetically acceptable aqueous carrier;
(c) a gel network;
wherein the near-terminal branched compound is not comprised in a gel network.

According to a fourth aspect, the present invention relates to the use of the personal care composition according to the first aspect for conditioning hair.

According to a fifth aspect, the present invention relates to a method of conditioning hair comprising applying the personal care composition according to the first aspect onto hair.

DETAILED DESCRIPTION OF THE INVENTION

In all embodiments of the present invention, all percentages are by weight (wt %) of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the number average molecular weight unless otherwise stated.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Herein, "comprising" means that other steps and other ingredients which do not affect the end result can be added. This term encompasses the terms "consisting" or and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

The term "substantially free from" or "substantially free of" as used herein means less than about 1 wt %, preferably less than about 0.8 wt %, more preferably less than about 0.5 wt %, still more preferably less than about 0.3 wt %, even more preferably less than about 0.1 wt %, most preferably about 0 wt %, by total weight of the composition.

"Hair," as used herein, means mammalian hair including scalp hair, facial hair and body hair, more preferably hair on the human head and scalp. "Hair shaft" means an individual hair strand/fibre and may be used interchangeably with the term "hair."

As used herein, "near-terminal branched compounds" means a compound with one, two, or three $(C_1-C_3)$alkyl branches on a carbon atom within 40% of the non-functionalized end of the longest chain. The functionalized end of the near-terminal branched fatty acids, fatty alcohols, and derivatives of fatty acids and alcohols is that which contains the acid, alcohol, or derivative moieties. The non-functionalized carbon at the end of carbon backbone is referred to as the 'omega' position. For example, near-terminal branched compounds that are 10 carbon atoms in length can have branching up to the omega-3 position, while near-terminal branched compounds that are 30 carbon atoms in length can have branching up to the omega-11 position. The near-terminal branched compounds of the invention typically have branching at the omega-1, omega-2, omega-3, omega-4, omega-5, and/or omega-6 positions of the compound (illustrated in the structure below), depending on the length of the compound, preferably at the omega-1, omega-2, and/or omega-3 positions, more preferably at the omega-1 and/or omega-2 positions.

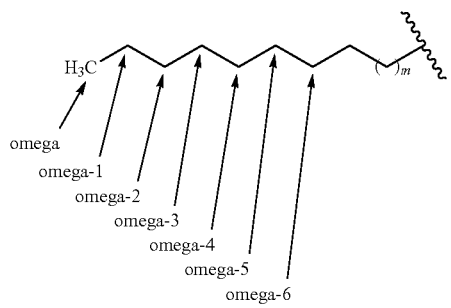

Near-terminal branched compounds with branching at the omega-1 position are referred to as "iso". Near-terminal branched compounds with branching at the omega-2 position are referred to as "anteiso". For example, a compound with 10 carbon atoms in its carbon backbone with a methyl branch at the omega-1 position: the branch is within 40% of the non-functionalized end of the carbon chain (e.g., 2/10× 100%=20%) and is referred to as near-terminal branched. In contrast, a compound with 10 carbon atoms in its carbon backbone and methyl branch at the omega-4 position—the branch is not within 40% of the non-functionalized end of the carbon chain (e.g., 5/10×100%=50%) and so is not referred to as "near-terminal branched."

As used herein, "linear compounds" are free of branches on the carbon backbone.

As used herein, "mid-chain compounds" contain alkyl branches on a carbon atom that is between about 40% to about 60% of the non-functionalized end of the longest carbon chain. For example, a mid-chain branched compound that is 12 carbon atoms in length can have branching on the omega-5 and/or omega-6 position. A mid-chain branched compound that is 30 carbon atoms in length can have branching on the omega-12 to the omega-17 position.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Carbon backbone", as used herein, means the longest carbon chain in the compound.

"Derivatives," as used herein, includes but is not limited to, amide, ether, ester, amino, carboxyl, acetyl, and/or alcohol derivatives of a given compound.

The term "charge density", as used herein, refers to the ratio of the number of positive charges on a polymer to the molecular weight of said polymer.

The inventors have surprisingly found that the personal care composition pursuant to the present invention provides dry conditioning/dry combing benefits comparable in performance to both large and small particle silicones, including polydimethylsiloxanes and dimethiconols. The personal care composition may effect the conditioning via a coacervate-based deposition mechanism, which provides excellent conditioning performance, for example in the context of a conditioning shampoo formulation. Further advantages of the present invention include: conditioning across hair types (effective on lift/damaged, Asian and virgin brown hair); the near-terminal branched compound can be naturally derived, i.e. alcohol or fatty acid precursor may be from a renewable source; the sensory profile is also felt to be lighter/softer than silicone ("clean feel") and less greasy than provided by emollient esters; the near-terminal branched compound is highly compatible with the requirements of a compacted formulation; and the near-terminal branched compound is not comprised in a gel network and does not disrupt gel networks, which typically provide the wet conditioning benefits of a conditioning formulation—consequently the present invention allows excellent dry conditioning benefits without reducing any wet conditioning benefits.

18-methyl eicosanoic acid (18-MEA) is a lipid naturally present on the outside of the hair cuticle, which lubricates the hair. 18-MEA is a carboxylic acid comprising 20 carbon atoms with a methyl group at the 18 position, which is the 2-omega or anteiso position. Without being bound by theory, the inventors believe that near-terminal branched compound can acts as a mimic of 18-MEA and thus 'top-up' the natural lubricant of the hair. Consequently the reduced friction benefits result when hair is treated with the present invention. The inventors believe that this is due to a reduction in surface energy (reduction in inter-fiber friction).

The present invention also provides the opportunity to at least reduce silicone amount when used in combination with the near-terminal branched compound as described herein. In combination with low levels of silicone, the inventors believe that the near-terminal branched compound likely enhances intrinsic deposition efficiency of silicones in a conditioning shampoo. Consequently, the compositions and formulations of the present invention represent more sustainable technology in comparison to conventional silicone-driven conditioning formulations.

18-methyl eicosanoic acid (18-MEA) is a lipid naturally present on the outside of the hair cuticle, which lubricates the hair. 18-MEA is a carboxylic acid comprising 20 carbon atoms with a methyl group at the 18 position, which is the 2-omega or anteiso position. Without being bound by theory, the inventors believe that the near-terminal branched compound acts as a mimic of 18-MEA. Consequently the reduced friction benefits result when hair is treated with the present invention. The inventors believe that this is due to a reduction in surface energy and a corresponding reduction in inter-fiber friction.

According to the first aspect, the present invention relates to a personal care composition comprising: a near-terminal branched compound according to Formula I as described above. In an embodiment, the composition comprises at least two different near-terminal branched compounds according to Formula I above and wherein neither said near-terminal branched compounds are comprised in a gel network. In an embodiment, wherein when Y is null, the substituent Z is attached to directly m.

The near-terminal branched compound is not comprised in a gel network. The near-terminal branched compound should be compatible with a gel network found in conditioner formulations such that the near-terminal branched compound should not disrupt/solubilize ordered lamellar structure of the gel network since the gel network this a primary source of wet feel and wet combing benefits. In an embodiment, the composition is substantially free of near-terminal branched compounds as defined above, which are comprised in and/or disrupt the lamellar structure of the lamellar gel network. The presence of a gel network or gel matrix can be can be measured by various test methods including SAXS and DSC (Differential Scanning Calorimetry) analytical test methods.

In an embodiment, the composition comprises about 1 wt % or less, or about 0.75 wt % or less, or about 0.5 wt % or less, or about 0.25 wt % or less, or about 0% of a silicone compound, by total weight of the composition. This is because the near-terminal branched compound is a conditioning active and can replace, at least partially, the use of a silicone compound for conditioning purposes. In an embodiment, the silicone compound is a conditioning silicone compound selected from the group consisting of: polydimethylsiloxanes, dimethiconols, aminosilicones, and mixtures thereof. In an embodiment, the silicone compound is a terminal aminosilicone.

In an embodiment, the near-terminal branched compound is according to Formula I as described above, wherein Z is a monovalent substituent selected from the group consisting of: —O(C=O)R$^3$, —COOR$^3$; wherein R$^3$ is either:
  i) a linear alkyl or alkenyl comprising a carbon chain of 8 to 24 carbons, or
  ii) a near-terminal branched alkyl chain according to Formula II

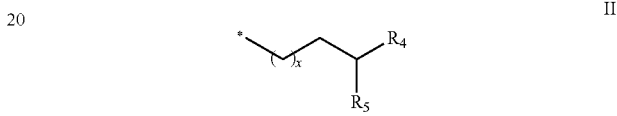

wherein R$^4$ is methyl, ethyl or propyl; R$^5$ is methyl, ethyl or propyl; x is alkyl or alkenyl
comprising a carbon chain of 5 to 19 carbons.

In an embodiment, m and/or x comprises a carbon chain of 7 to 19, preferably is 9 to 19, more preferably 11 to 18, most preferably 12 to 17 carbons; and Y is null. In an embodiment, m and/or x comprises a saturated carbon chain. In an embodiment, the carbon chain of m and/or x comprises 1 to 3 branches wherein each branch is selected from the group consisting of methyl, ethyl and propyl.

In an embodiment, the near-terminal branched compound is synthesized by metathesis. See synthesis mechanisms below. In an embodiment, at least 50%, or at least 60%, or at least 70%, or at least 85% of said near-terminal branched compound is derived from natural feedstocks. In an embodiment, at least 50% of said near-terminal branched compound is not derived from petroleum.

In an embodiment, the near-terminal branched compound is a wax ester selected from the group consisting of: 13-methylhexadecylpalmitate, 15-methylhexadecylstearate, 14-methylhexadecyl stearate; 14-methylhexadecyl palmitate; 16-methyloctadecyl stearate; 16-methyloctadecyl palmitate; 12-methyltetradecyl stearate; 12-methyltetradecylpalmitate; 18-methyleicosyl stearate; 18-methyleicosyl palmitate; 13-methylhexadecyl palmitate; 13-methylhexadecyl stearate; 15-methylhexadecyl stearate; 15-methylhexadecyl palmitate; 13-methyltetradecyl stearate; 14-methylhexadecanoic acid, tetradecyl ester; 14-methylhexadecanoic acid, hexadecyl ester; 14-methylhexadecanoic acid, octadecyl ester; 16-methyloctadecanoic acid, hexadecyl ester; 18-methyleicosanoic acid, hexadecyl ester; 18-methyleicosanoic acid, tetradecyl ester; 13-methylhexadecyl palmitate, 13-methylhexadecyl stearate; 15-methylhexadecanoic acid, tetradecyl ester; 15-methylhexadecanoic acid, hexadecyl ester; 17-methyloctadecanoic acid, hexadecyl ester, and mixtures thereof.

In an embodiment, the near-terminal branched compound is selected from esters being in viscous liquid form, semi-solid form, soft-solid form, wax form, and also mixtures thereof. This is in view of providing optimal rheology, melting transitions, and viscoelastic profiles for allowing deposition of the conditioning agents onto hair in combination with the near-terminal branched compound not being comprised in a gel network.

In an embodiment, the near-terminal branched compound is a near terminal-branched wax ester. "Wax", as used herein, means a viscous or semi-solid material of natural origin: characteristically lustrous, insoluble in water, and having a low softening temperature, comprising a high proportion of esters of fatty acids. In an embodiment, the near terminal-branched wax ester comprises 13 to 22 carbon atoms in the fatty acid portion and 14 to 22 carbon atoms in the alcohol/ester portion.

Wax esters can be prepared by transesterification or via reaction of the fatty acid chloride component with the fatty alcohol or in accordance with other methods also well known in the art. They can also be prepared by metathesis of an existing unsaturated wax ester resulting in a near-terminal branched unsaturated wax ester of the invention. Hydrogenation by conventional means will yield a near-terminal branched saturated wax ester. See the section "synthesis mechanism".

In an embodiment of the invention, the wax ester compounds have a methyl or ethyl branch on the fatty acid portion of the wax ester, on the fatty alcohol portion of the wax ester, or on both portions of the wax ester. When a branch is present on both portions, the branches are at omega-1, omega-2 or omega-3, or a combination thereof.

In an embodiment, the branch is on the fatty alcohol portion of the wax ester. In an embodiment, the wax ester is selected from the group consisting of: 15-methylhexadecyl stearate; 15-methylhexadecyl palmitate; 13-methyltetradecyl stearate, 14-methylhexadecyl stearate; 14-methylhexadecyl palmitate; 16-methyloctadecyl stearate; 16-methyloctadecyl palmitate; 12-methyltetradecyl stearate; 12-methyltetradecylpalmitate; 18-methyleicosyl stearate; 18-methyleicosyl palmitate, 13-methylhexadecyl palmitate; 13-methylhexadecyl stearate, and mixtures thereof. In an embodiment, the branch is on the fatty acid portion of the wax ester. In an embodiment, the wax ester is selected from the group consisting of: 15-methylhexadecanoic acid, tetradecyl ester; 15-methylhexadecanoic acid, hexadecyl ester; 17-methyloctadecanoic acid, hexadecyl ester, 14-methylhexadecanoic acid, tetradecyl ester; 14-methylhexadecanoic acid, hexadecyl ester; 14-methylhexadecanoic acid, octadecyl ester; 16-methyloctadecanoic acid, hexadecyl ester; 18-methyleicosanoic acid, hexadecyl ester; 18-methyleicosanoic acid, tetradecyl ester, 13-methylhexadecyl palmitate, 13-methylhexadecyl stearate, and mixtures thereof.

The personal care composition comprises a cosmetically acceptable aqueous carrier. The composition may be in the form of a pourable liquid (pourable when under ambient conditions). The cosmetically acceptable aqueous carrier may be present at a level of from about 20% to about 95%, more preferably from about 60% to about 85%. In an embodiment the composition comprises a cosmetically acceptable aqueous carrier and is in the form of a pourable liquid. The carrier may comprise water, or a miscible mixture of water and organic solvent, but preferably comprises water with minimal or no significant concentrations of organic solvent, except as otherwise incidentally incorporated into the composition as minor ingredients of other essential or optional components. Suitable carriers may be selected from the group consisting of water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

According to the second aspect, the present invention relates to a conditioning shampoo formulation for cleansing hair comprising:
(a) a near-terminal branched compound as defined in the first aspect;
(b) a cosmetically acceptable aqueous carrier;
(c) a cationic polymer;
(d) anionic surfactant;
wherein the near-terminal branched compound is not comprised in a gel network.

The embodiments vis-à-vis the near-terminal branched compound described above apply to the conditioning shampoo formulation.

The conditioning shampoo formulation comprises an anionic surfactant. The formulation may comprise from about 0.01% to about 20%, or from about 0.1% to about 5% anionic surfactant, by total weight of the formulation. The anionic surfactant may be the salt of an anionic surfactant comprising 12 to 14 carbon atoms. The anionic surfactant may be selected from the group consisting of: sodium lauryl sulfate, sodium laureth sulfate, sodium tridecyl sulfate, sodium trideceth sulfate, sodium myristyl sulfate, sodium myreth sulfate, and mixtures thereof.

The formulation may further comprise a co-surfactant. In an embodiment, the co-surfactant is an anionic co-surfactant, which may be present in amount of from about 0.01% to about 20%, or from about 0.1% to about 5%, by total weight of the formulation. The anionic co-surfactants may be selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and mixtures thereof. In an embodiment, the anionic co-surfactant is sodium lauryl sulfate or sodium laureth sulfate.

In an embodiment, the co-surfactant is selected from the group consisting of CAPB (cocoamidopropyl betaine), Cocobetaine (CocoB), sodium lauroylamphoacetate (NaLAA), laurylhydroxysultaine (LHS), cocomonoethanol amide (CMEA), and mixtures thereof.

The conditioning shampoo formulation comprises a cationic polymer. The formulation may comprise from about 0.05% to about 3%, or from about 0.075% to about 2.0%, or from about 0.1% to about 1.0% of cationic polymer, or from about 0.1% to about 0.5%, or from about 0.1% to about 0.25%, by total weight of the formulation. The cationic polymers may have cationic charge densities of from about 0.5 meq/gram to about 7 meq/gram, or from about 0.9 meq/gram to about 5 meq/gram, or from about 1.2 meq/gram to about 4 meq/gram, at the pH of intended use of the composition, which pH will generally range from about pH 3 to about pH 9, or between about pH 4 and about pH 8. Herein, "cationic charge density" of a polymer refers to the ratio of the number of positive charges on the polymer to the weight average molecular weight of the polymer. The weight average molecular weight of the cationic polymer may be between about 10,000 and 10 million, or between about 50,000 and about 5 million, or between about 100,000 and about 3 million.

Suitable cationic polymers may comprise cationic nitrogen-containing moieties such as quaternary ammonium or cationic protonated amino moieties. The counterion may be selected from the group consisting of halides (e.g., chloride, fluoride, bromide, iodide), sulfate, methylsulfate, and combinations thereof. The cationic polymer may be selected from the group consisting of polysaccharide polymers, cationic cassia, cationic guar gum derivatives, quaternary nitrogen-containing cellulose ethers, synthetic polymers, copolymers of etherified cellulose, guar and starch, and combinations thereof. The cationic polymer should be either soluble in the formulation or soluble in a complex coacervate phase in the composition formed by the cationic polymer and an anionic, amphoteric and/or zwitterionic surfactant. Complex coacervates of the cationic polymer can also be formed with other charged materials in the formulation.

The cationic polymer may be selected from the group consisting of: polyquaternium-10; a cationic guar; a cationic acrylamide; polyquaternium-76; polyquaternium-6, and mixtures thereof.

In an embodiment, the conditioning shampoo formulation comprises a gel network. In an embodiment, the conditioning shampoo formulation comprises up to about 3 wt %, or from about 1 to about 2% of a gel network, by total weight of the conditioning shampoo formulation. In an embodiment, the gel network is a dispersed gel network phase. Dispersed gel network phases are discussed in US2007/0110700A1. In an embodiment, the conditioning shampoo formulation comprises a dispersed gel network phase comprising: at least about 0.05% of a fatty alcohol, or from about 0.05% to about 3%, or from about 0.05% to about 2%; at least about 0.01% of a surfactant; by weight of said formulation. The fatty alcohol may have a negative impact on lather when present at more than about 5% by total weight of said formulation. The dispersed gel network phase may comprise water. The fatty alcohol fatty may be selected from fatty alcohols having from about 18 to about 70 carbon atoms. In an embodiment of the dispersed gel network phase, the surfactant is present relative to the fatty alcohol at a weight ratio from about 1:5 to about 5:1. In an embodiment, conditioning shampoo formulation comprises a dispersed gel network phase comprising either: a linear fatty alcohol and an anionic surfactant, or a linear fatty alcohol and a cationic surfactant.

The shampoo formulation may further comprise: water soluble vitamins and their derivatives, water soluble amino acids and their salts and/or derivatives, viscosity modifiers, dyes, nonvolatile solvents or diluents (water soluble and insoluble), pearlescent aids, thickeners, foam boosters, additional surfactants or nonionic co-surfactants, pediculocides, pH adjusting agents, perfumes, preservatives, chelants, proteins, skin active agents, sunscreens, UV absorbers, vitamins, niacinamide, caffeine and minoxidil. The shampoo formulation may comprise from about 0% to about 5% vitamins and amino acids, by total weight of the shampoo formulation. The shampoo formulation may also comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I. Names. The shampoo formulation may comprise from about 0% to about 5% pigment materials. The shampoo formulation may comprise from about 0% to about 5% antimicrobial agents. The shampoo formulation may have a pH of from about 6 to about 10, or from about 7 to about 10, or from about 7 to about 9.

The conditioning shampoo formulation may also comprise an anti-dandruff active. The anti-dandruff active may be selected from the group selected from the group consisting of: antimicrobial actives, pyridinethione salts, azoles, selenium sulfide, particulate sulfur, keratolytic acid, salicylic acid, octopirox (piroctone olamine), coal tar, and combinations thereof. The composition may comprise zinc pyridinethione (ZPT). Pyridinethione anti-dandruff agents are described, for example, in U.S. Pat. No. 2,809,971. The concentration anti-dandruff active may be from about 0.01 wt % to about 5 wt %, or from about 0.1 wt % to about 3 wt %, or from about 0.1 wt % to about 2 wt %, by total weight of the conditioning shampoo formulation.

In an embodiment, the conditioning shampoo formulation comprises coacervates. Coacervates are separated phases comprised of cationic polymer and anionic surfactant, and are typically generated under dilution of the conditioning shampoo composition. This separated phase entraps/encapsulates the conditioning agent to be deposited. Coacervate complexes may also be pre-formed from cationic polymers and anionic surfactants and added as a dispersed phase. The near-terminal branched compound is a conditioning agent. In general, the efficiency of this encapsulation and subsequent deposition on the hair substrate, increase as the particle size of the benefit agent decreases. When formulated as an emulsified particle, the average diameter of the particles may be less than about 5 microns, or less than about 2 microns, or less than about 1 micron, or from about 0.1 to about 0.2 microns. For translucent and/or transparent conditioning shampoo formulations, the average diameter of the particles may be less than about 0.1 micron, or from about 0.03 to about 0.05 microns.

In a further embodiment of the conditioning shampoo formulation, the conditioning agent is deposited by a filtration mechanism. The near-terminal branched compound is a conditioning agent. In an embodiment, the conditioning shampoo formulation comprises near-terminal branched compound comprised in discrete particles/droplets. In this embodiment, the average diameter of the particles/droplets may be greater than 10 microns, or greater than 20 microns, or from about 30 to about 50 microns.

According to the third aspect, the present invention relates to a rinse-off conditioner formulation comprising:
  (a) a near-terminal branched compound as defined in the first aspect;
  (b) a cosmetically acceptable aqueous carrier;
  (c) a gel network;
wherein the near-terminal branched compound is not comprised in a gel network.

In an embodiment of the third aspect, gel network comprises a fatty alcohol and a cationic surfactant. In an embodiment of the third aspect, the gel network comprises a linear fatty alcohol and a quaternary ammonium compound. In an embodiment, the rinse-off conditioner formulation comprises up to about 10%, up to about 8% of a gel network, by total weight of the formulation. The details herein vis-à-vis the first and second aspects may also apply to the third aspect.

According to the fourth aspect, the present invention relates to the use of the personal care composition according to the first aspect for conditioning hair. An embodiment relates to the use of the conditioning shampoo formulation according to the second aspect for conditioning hair. An embodiment relates to the use of the rinse-off conditioner formulation according to the third aspect for conditioning hair. The details herein vis-à-vis the first, second and third aspects also apply to the fourth aspect.

According to the fifth aspect, the present invention relates to a method of conditioning hair comprising applying the personal care composition according to the first aspect onto hair. An embodiment relates to a method of conditioning hair comprising applying the conditioning shampoo formulation according to the second aspect onto hair. An embodiment relates to a method of conditioning hair comprising applying the rinse-off conditioner formulation according to the second aspect onto hair. The details herein vis-à-vis the first, second and third aspects also apply to the fifth aspect.

Synthesis Mechanism

The branched compounds may be synthesized by metathesis. Useful mechanisms are also discussed in Suguro and Mori (1979), *Agric. Biol. Chem.*, 43 (4), 869; Yuasa and Tsuruta (2004), *Flavour Fragr. J.*, 19, 199. Furthermore, production via genetically engineered bacteria is described in US2010/0105955; US2010/0105963; WO2007/136752; WO2008/119082; WO2009/111672; and US61/289,039.

Metathesis of Glyceryl Trioleate with
3-Methyl-1-Hexene, 4-Methyl-1-Hexene and
4-Methyl-1-Pentene to Prepare Near-Terminal
Branched Alcohols

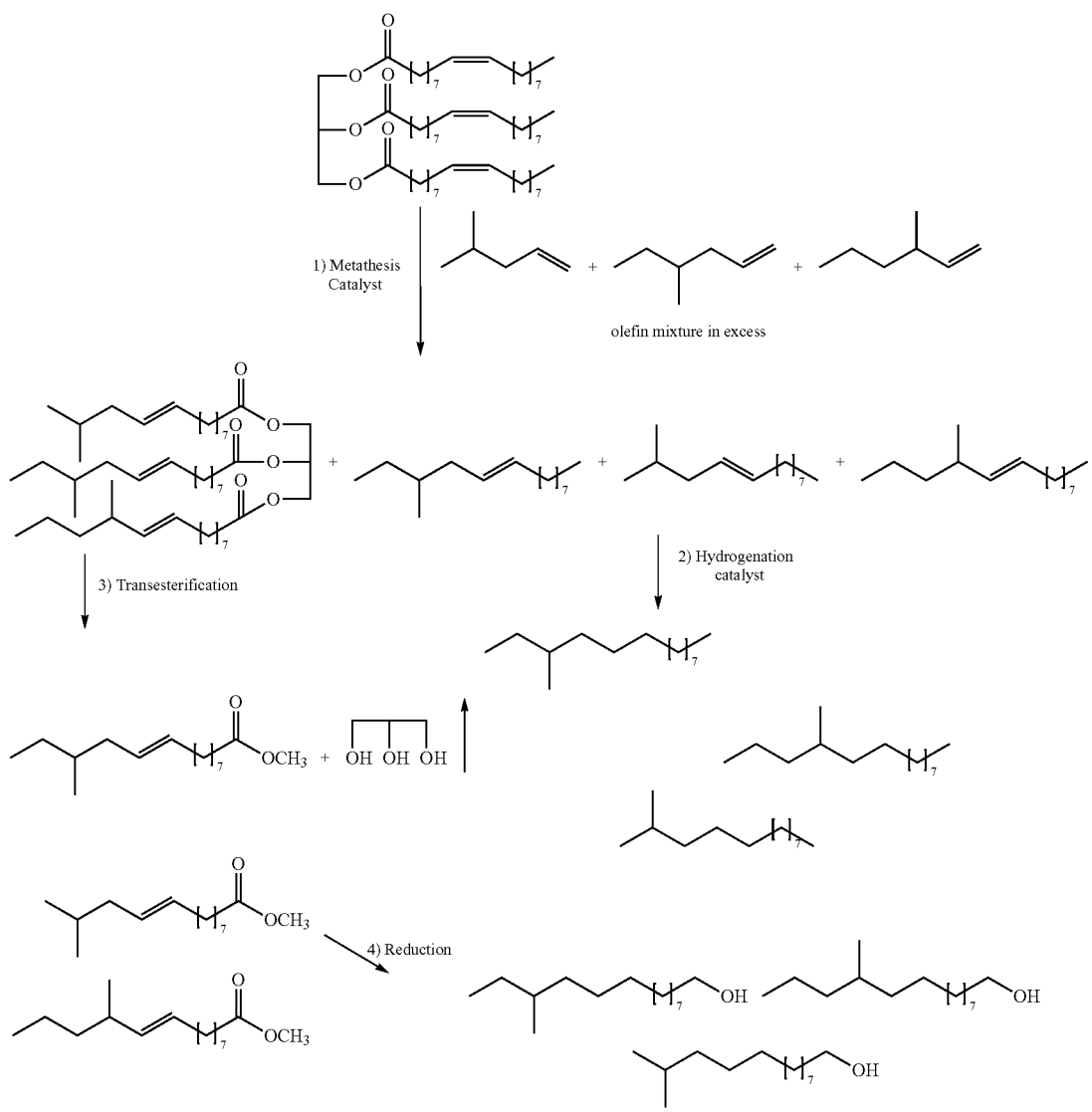

Scheme 1.

Reactants and subsequent products thereof can be derived from the oils: trioleate (shown in Scheme 1), soybean (hydrogenated), rapeseed, canola, palm, palm kernel, coconut, jatropha, high erucic rapeseed, cottonseed, tallow, yellow grease, corn, sunflower, babasu, and mixtures thereof. The olefin used in the metathesis reaction can be a single branched olefin, a mixture of branched olefins or a mixture of branched olefins with other nonreactive impurities such as aromatic alkyls, paraffins, branched paraffins and cycloalkanes.

I.A. Synthesis of Mixture of Near-Terminal Branched Alcohols:

About 8.854 g (0.010 mol) of glyceryl trioleate (Sigma catalog #T7140) and 25 mL of hexane are placed in a 316 stainless steel stirred pressure vessel. Solvent and gylceryl trioleate are predried over 4A molecular sieves prior to introduction to vessel. About 0.0006 mol of tungsten hexachloride and 0.0006 mol of tetramethyl tin is added to the vessel. The reactor is sealed, stirred, and purged several times with $N_2$. About 0.030 mol of a blend of 3-methyl-1-hexene, 4-methyl-1-hexene and 4-methyl-1-pentene is added to the vessel under $N_2$. The stirred mixture is heated to 220° C. under 100 psig $N_2$ and maintained at this temperature for several hours. The reactor is cooled and the product removed. The reaction mixture is quenched with 2-3 mL of concentrated ammonium hydroxide and extracted with additional 10 mL hexane. The hexane and any volatile olefins remaining are stripped on a rotary evaporator. The remaining product is subjected to fractional distillation to remove the remaining non volatile olefin mixture. This branched olefin mixture containing mainly a mixture of 1'-methyl-9-tetradecene, 12-methyl-9-tridecene and 12-methyl-9-tetradecene is hydrogenated under standard reaction conditions to provide a high quality semi-biodiesel fuel with branching. The bottom of the flask from distillation contains mainly the new branched triglyceride mixture. This new triglyceride mixture is subjected to standard transesterification conditions in the presence of methanol and a catalytic amount of sodium hydroxide or sodium methoxide in methanol. The mixture phase separates into glycerine (bottom phase) and a mixture of methyl esters (top phase) consisting mainly of 12-methyl-9-tetradecenoic acid methyl ester, 12-methyl-9-tridecenoic acid methyl ester and 1'-methyl-9-tetradecenoic acid methyl ester. The unique branched methyl ester mixture is reduced using standard procedures with copper chromite catalyst in the presence of hydrogen to give essentially a mixture of 12-methyltetradecan-1-ol, 12-methyltridecan-1-ol and 11-methyltetradecan-1-ol. The mixture is vacuum distilled to provide a purified mixture.

I.B. Esterification: Preparation of 12-methyltetradecyl palmitate:

A dry 500 ml 3-neck round bottom flask fitted with a condenser is charged with 12-methyltetradecan-1-ol (10.0 g, 0.0438 mol) from example I.A, 125 ml diethyl ether, triethylamine (4.87 g, 0.0481 mol), and 4-(dimethylamino)pyridine (DMAP) 0.5350 g, 0.0044 mol). The solution is stirred at room temperature under a positive $N_2$ atmosphere. Palmitoyl chloride (13.20 g, 0.0481 mol) in 13 ml diethyl ether is added dropwise to the reaction flask from an addition funnel at room temperature. A thick white precipitate forms. An additional 115 ml of diethyl ether is added to help stirring the thick slurry. The mixture is stirred overnight at room temperature under a nitrogen atmosphere. After 18 hours reaction time an aliquot of the mixture is spotted on a TLC plate (95:5 v/v hexane:ethyl acetate) versus the starting materials, indicating the reaction to be complete. The reaction mixture is vacuum filtered, and the filter cake rinsed with 2×400 ml diethyl ether. The filtrate is back extracted with 2×400 ml water. The ether phase is dried with anhydrous magnesium sulfate, vacuum filtered and the filtrate concentrated in vacuo on a rotary evaporator at 40° and the crude product recovered (20.3 g). The crude product is dissolved in warm ethanol (150 ml) and placed into a freezer to recrystallize the product. The precipitated product is vacuum filtered and the filter cake rinsed with 0° C. ethanol (3×50 ml). The cake is further dried in vacuo at room temperature to yield 12-methyltetradecyl palmitate as a white powdery solid (17.3 g). Yield 84.1%.

I.C. Near-Terminal Branched Alcohol Ethoxylate:

223.7 grams (1.0 mol) of the near terminal alcohol mixture of Example I.A. above plus sufficient catalyst to facilitate the reaction of the alcohol with ethylene oxide within a suitable period of time and in a controllable manner are charged to a 600 mL stainless steel stirred pressure vessel with a cooling coil. A suitable catalyst is 1.1 grams of a solution consisting of 50% potassium hydroxide in water. Other kinds and quantities of catalyst can be used. The reactor is heated while applying a vacuum for removing materials that can result in side products, such as water, that may be introduced with the catalyst, at a temperature that does not allow the loss of the near terminal alcohol mixture of example I.A., generally between 40° C. and 90° C., but preferably between about 60° C. and about at 80° C., when using a water aspirator as a vacuum source. The removal of water is facilitated by using low speed agitation, generally about 50 rpm, while sparging the mixture with a low level (trickle) stream of inert gas either through a bottom drain valve or through a stainless steel gas dispersion frit or any inert dip-tube or sintered metal fritted material or by sweeping the area above the mixture with inert gas. Samples can be drawn from the reactor and analyzed for water content using an appropriate analytical method such as Karl-Fischer titration. After completion of the water removal step, ethylene oxide can be added all at once if the reactor system is properly designed to prevent an uncontrolled rate of reaction. However, the best reaction control is obtained by first heating the reactor under a static vacuum (or optionally with added pressure from an inert gas such as $N_2$) to a temperature that is suitable for the reaction of the alcohol-catalyst mixture with ethylene oxide to occur with minimum side products and color generation, generally between 85° and 150° C., but preferably between about 110° C. and 130° C. Once the reactor has reached the desired temperature, 308 grams (7.0 mol) of ethylene oxide is added at a rate that will be controllable by the cooling system, generally over a period of 30 to 60 mins. After the addition of ethylene oxide is completed, stirring and heating is continued until the ethylene oxide has been consumed by the reaction. The product can then be degassed and removed from the reaction vessel and stored as is or for long term storage the catalyst is neutralized with one equivalent of an acid selected from citric, HCl or sulfuric acid. The neutralized product can be filtered to remove any solid residue.

SHAMPOO EXAMPLES

All units without numbers are in wt %; QSP=sufficient quantity for 100%.

Example Table 1

Conditioning Shampoo Formulations being Substantially Free of Silicone

| Formulation/Ingredient | A | B | C |
| --- | --- | --- | --- |
| Water | QSP | QSP | QSP |
| 14-Methylhexadecyl stearate[1] | 0.5 to 2.0 | — | 0.25 to 1.0 |
| 16-Methyloctadecyl palmitate[1] | — | 0.5 to 2.0 | 0.25 to 1.0 |
| Cationic Guar[2] | 0.25 | 0.25 | 0.25 |
| Sodium Laureth Sulfate[3] | 8.5 | 8.5 | 8.5 |
| Sodium Lauryl Sulfate[4] | 6.5 | 6.5 | 6.5 |
| CMEA[5] | 0.8 | 0.8 | 0.8 |
| Cocoamidopropyl Betaine[6] | 2.0 | 2.0 | 2.0 |
| Fragrance | 0.70 | 0.70 | 0.70 |
| Preservatives, pH, viscosity adjustment | Up to 3% | Up to 3% | Up to 3% |

KEY:
[1] = Wax esters prepared according to synthesis above, formulated as 1 micron emulsions;
[2] = Jaguar Excel, from Rhodia;
[3] = Sodium Laureth-3 Sulfate, from Procter & Gamble (P&G);
[4] = Sodium Lauryl Sulfate, from P&G;
[5] = Ninol Comf, from Stepan;
[6] = Amphosol HCA-B, from Stepan.

Example Table 2

Comparative Conditioning Shampoo Formulations

| Formulation/Ingredient | Shampoo Base | Silicone Control A | Silicone Control B | D | E | F |
|---|---|---|---|---|---|---|
| Water | QSP | QSP | QSP | QSP | QSP | QSP |
| 14-Methylhexadecyl stearate[1] | — | — | — | 1.01-1.35 | — | — |
| 16-Methyloctadecyl palmitate[1] | — | — | — | — | 1.0-1.35 | — |
| 12-Methyltetradecyl palmitate[1] | — | — | — | — | — | 1.0-1.35 |
| Silicone (1 micron)[2] | — | 1.0-1.35 | — | — | — | — |
| Silicone (30 microns)[2] | — | — | 1.0-1.35 | — | — | — |
| Cationic Guar[3] | 0.05 | 0.05 | 0.05 | 0.05 | 0.05 | 0.05 |
| Sodium Laureth Sulfate[4] | 10.5 | 10.5 | 10.5 | 10.5 | 10.5 | 10.5 |
| Sodium Lauryl Sulfates[5] | 1.5 | 1.5 | 1.5 | 1.5 | 1.5 | 1.5 |
| CMEA[6] | 0.8 | 0.8 | 0.8 | 0.8 | 0.8 | 0.8 |
| Cocoamidopropyl Betaine[7] | 1.0 | 1.0 | 1.0 | 1.0 | 1.0 | 1.0 |
| Fragrance | 0.70 | 0.70 | 0.70 | 0.70 | 0.70 | 0.70 |
| Preservatives, pH, viscosity adjustment | Up to 3% | Up to 3% | Up to 3% | Up to 3% | Up to 3% | Up to 3% |

KEY:
[1] = Wax esters prepared according to synthesis above, added as 1 micron emulsions;
[2] = 330000 cSt PDMS, from Momentive;
[3] = Jaguar Excel, from Rhodia;
[4] = Sodium Laureth-1 Sulfate, from P&G;
[5] = Sodium Lauryl Sulfate, from P&G;
[6] = Ninol Comf, from Stepan;
[7] = Amphosol HCA-B, from Stepan.

Example Table 3

Gel Network Conditioning Shampoo Formulations

| Formulation Ingredient | G | H | I | J | K | L |
|---|---|---|---|---|---|---|
| Sodium Laureth Sulfate[1] | 10.5 | 10.5 | 10.5 | 10.5 | 10.5 | 10.5 |
| Sodium Lauryl Sulfate[2] | 1.5 | 1.5 | 1.5 | 1.5 | 1.5 | 1.5 |
| CMEA[3] | 0.8 | 0.8 | 0.8 | 0.8 | 0.8 | 0.8 |
| Cocoamidopropyl Betaine[4] | 1.0 | 1.0 | 1.0 | 1.0 | 1.0 | 1.0 |
| Cationic Guar[5] or PQ-76[6] | 0.25 | 0.25 | 0.25 | 0.25 | 0.25 | 0.25 |
| Gel Network[7] | 1.0-2.0* | 1.0-2.0* | 1.0-2.0* | 1.0-2.0* | 1.0-2.0* | 1.0-2.0* |
| 14-Methylhexadecyl stearate[8] | 1.0-2.0 | — | — | 1.0-2.0 | — | — |
| 16-Methyloctadecyl palmitate[8] | — | 1.0-2.0 | — | — | 1.0-2.0 | — |
| 12-Methyltetradecyl palmitates[8] | — | — | 1.0-2.0 | — | — | 1.0-2.0 |
| EGDS[9] | 1.50 | 1.50 | 1.50 | 1.50 | 1.50 | 1.50 |
| Fragrance | 0.70 | 0.70 | 0.70 | 0.70 | 0.70 | 0.70 |
| Preservatives, pH, viscosity adjustment | Up to 3% | Up to 3% | Up to 3% | Up to 3% | Up to 3% | Up to 3% |
| Water | QSP | QSP | QSP | QSP | QSP | QSP |

KEY:
[1] = Sodium Laureth-1 Sulfate, from P&G;
[2] = Sodium Lauryl Sulfate, from P&G;
[3] = Ninol Comf, from Stepan;
[4] = Amphosol HCA-B, from Stepan;
[5] = NHance-3205, from Aqualon;
[6] = Polyquaternium-76, from Rhodia;
[7] = Gel Network actives disclosed in US20070110700A1;
[8] = Wax esters prepared according to synthesis above;
[9] = Ethyleneglycol distearate;
*= The gel network is added as a dispersed phase and is expressed herein as active percent of fatty amphiphile or fatty amphiphile plus cationic surfactant.

CONDITIONER EXAMPLES

All units without numbers are in wt %; QSP=sufficient quantity for 100%.

Example Table 4

Rinse-Off Conditioner Formulations

| Formulation Ingredient | Control | A | B | C | D |
|---|---|---|---|---|---|
| Water | QSP | QSP | QSP | QSP | QSP |
| Behentrimonium Methosulfate/IPA | 2.2 | 2.2 | 2.2 | 2.2 | 2.2 |
| Ethylenediaminetetraacetic acid (EDTA) | 0.12 | 0.12 | 0.12 | 0.12 | 0.12 |
| Cetyl Alcohol | 1.5 | 1.5 | 1.5 | 1.5 | 1.5 |
| Stearyl Alcohol | 3.7 | 3.7 | 3.7 | 3.7 | 3.7 |
| Benzyl Alcohol | 0.4 | 0.4 | 0.4 | 0.4 | 0.4 |
| Preservative (e.g., KATHON ™ CG)$^x$ | 0.03 | 0.03 | 0.03 | 0.03 | 0.03 |
| 14-Methylhexadecyl stearate | — | 0.5-2.0 | — | 0.5-2.0 | — |
| 14-Methylhexadecyl palmitate | — | — | 0.5-2.0 | — | 0.5-2.0 |
| Amodimethicone | 0.5 | — | — | 0.25 | 0.25 |
| Pathenol | 0.1 | 0.1 | 0.1 | 0.1 | 0.1 |
| Perfume | 0.4 | 0.4 | 0.4 | 0.4 | 0.4 |

KEY:
$^x$ = blend of methylchloroisothiazolinone and methylisothiazolinone.

Example Table 5

Rinse-Off Conditioner Compositions

| Formulation Ingredient | Control | E | F | G | H |
|---|---|---|---|---|---|
| Water | QSP | QSP | QSP | QSP | QSP |
| EDTA | 0.13 | 0.13 | 0.13 | 0.13 | 0.13 |
| Stearyl Alcohol | 2.3 | 2.3 | 2.3 | 2.3 | 2.3 |
| Cetyl Alcohol | 0.9 | 0.9 | 0.9 | 0.9 | 0.9 |
| VARISOFT ® 432PPG $^y$, quaternary ammonium di-alkyl solution | 0.5 | 0.5 | 0.5 | 0.5 | 0.5 |
| Behentrimonium Methosulfate/IPA | 1.4 | 1.4 | 1.4 | 1.4 | 1.4 |
| Benzyl Alcohol | 0.4 | 0.4 | 0.4 | 0.4 | 0.4 |
| Preservative (e.g., KATHON ™ CG $^x$) | 0.03 | 0.03 | 0.03 | 0.03 | 0.03 |
| 12-Methyltetradecyl palmitate | — | 0.5-2.0 | — | 0.5-2.0 | — |
| 13-Methylhexadecyl stearate | — | — | 0.5-2.0 | — | 0.5.-2.0 |
| Amodimethicone | 0.8 | — | — | 0.4 | 0.4 |
| Pathenol | 0.1 | 0.1 | 0.1 | 0.1 | 0.1 |
| Perfume | 0.3 | 0.3 | 0.3 | 0.3 | 0.3 |

KEY:
$^y$ = dicetyldimonium chloride (~68% active) in propylene glycol and water;
$^x$ = blend of methylchloroisothiazolinone and methylisothiazolinone.

Composition/Formulation Preparation

Wax ester emulsions can be prepared by typical emulsion preparation procedures and typically have a 1 micron emulsion droplet size. On the small scale for laboratory samples a solid sample is weighed into Flack Tek Speedmixer cup at a level to represent 50% of the final mixture. NEODOL® 1-5 is added at a level to represent 5% of the final mixture. This combination is heated until the wax ester material has liquefied. The mixture is allowed to mix for 0.5 min on the speed-mixer at 2000 rpm Ammonium lauryl sulfate solution (28% active) is added at a level to represent about 10% of the final preparation any additional water required is added at this point, and the mixture re-heated to insure the wax ester material is again liquefied. The preparation in then mixed on the speed mixer for 5 mins at 3450 rpm. The particle size of the resulting emulsion is checked by simple light microscopy to insure it is in the right domain, e.g. about 1 micron.

On a larger scale the ammonium lauryl sulfate can be added to the de-ionized water amount required and the mixture heated to about 80° C. The wax ester material is combined with the NEODOL® 1-5 and the mixture heated until liquefied. This mixture is added in a controlled manor to aqueous ammonium lauryl sulfate solution with high speed mixing, e.g. a Divtech Eurostar with Turbine. The particle size is verified by light microscopy.

Comparative Data

Combing tests were carried out comparing formulations pursuant to the present invention with control formulations. The combing tests were carried as described in US2009/0246236A1 in paragraphs [0199] to [0202]. A non-conditioning clarifying shampoo serves as a "low" control (see below for formulation). A "high" control is treated with the same clarifying shampoo but followed by treatment with a standard silicone-containing rinse-off conditioner (formulation below). A typical 2-in-1 shampoo comprising silicone will typically provide medium to strong combing benefits on virgin brown hair, which approach the benefits of the high control, but only moderate benefits on low lift hair (i.e. bleach damaged hair). Efficacy of non-silicone technology can thus be subjectively assessed against these controls (and therefore vs. silicone).

This combing test method is representative of a typical consumer evaluation. Panelists are not experts but have several years experience of scoring formulations in such a way. The test is reproducible providing the same low and high controls are always used. The error for mean score is typically +/−1. A difference in 2 for the mean score is significantly different.

Low Control Clarifying Shampoo Formulation:

7.00 wt % Sodium Laureth-3 Sulfate; 0.14 wt % Tetrasodium EDTA; 1.11 wt % Citric Acid (Anhy.); 0.50 wt % Cocamide MEA; 0.03 wt % Kathon CG; 7.00 wt % Sodium Lauryl Sulfate; 0.10 wt % DMDM Hydantoin; 2.00 wt % Cocoamidopropyl Betaine; 0.70 wt % NaCl; 0.46 wt % Perfume; Distilled Water QSP.

High Control Silicone Conditioner Formulation:

0.64 wt % L-Glutamic Acid; 2.00 wt % Stearamidoproplydimethylamine; 2.50 wt % Cetyl Alcohol; 4.50 wt % Stearyl Alcohol; 4.20 wt % Dimethicone/Cyclomethicone (15/85 Blend); 0.10 wt % EDTA; 0.40 wt % Benzyl Alcohol; 0.33 wt % Kathon CG; 0.25 wt % Perfume; 0.225 wt % dl-Pantyl; 0.05 wt % dl-Panthenol; Water QSP. QSP=sufficient quantity for 100%.

The following formulas, 2-6, 9-13, 16-21 and 24-29, which are pursuant to the present invention, are as described in example table 2 above, with all esters added to the shampoo base as approximately one micron emulsions. Silicone and near-terminal branched compound deposition can be measured by Inductively Coupled Plasma Optical Emission Spectroscopy (ICP-OES). Silicone is extracted from hair samples with 50:50 toluene:methylisobutyl ketone and the extracted samples were compared to ICP calibration standards of known silicone concentration.

Virgin Brown Hair, Ease of Dry Combing—Body of Hair

| Sample | Formula | Mean Score | 95% LSD | | | D: Active |
|---|---|---|---|---|---|---|
| 1 | Low control | 1.88 | A | | | 0 |
| 2 | PDMS (30 microns)[1] | 5.50 | | B | | 78 |
| 3 | PDMS (1 micron)[1] | 8.63 | | | C D | 528 |
| 4 | C17 Anteiso ester[2] | 7.94 | | | C | 728 |
| 5 | Floraester 20[3] | 8.13 | | | C | 539 |
| 6 | Floraester 60[3] | 8.19 | | | C | 794 |
| 7 | High control | 8.25 | | | D | 84 |

KEY
[1]= 1.35% 330,000 cSt Polydimethylsiloxane (from Momentive);
[2]= 1.35% 14-methylhexadecylstearate;
[3]= 1.35% Jojoba esters (from Floratech);
D: Active = deposition of conditioning active i.e. silicone or near-terminal branched compound (units are ppm).

The conclusions from the comparative experiment (samples 1 to 7) include: Comparable dry combing benefits to silicones, including small particle emulsions. Deposition data confirms high deposition of near terminal/anteiso ester, comparable to small particle silicone. Performance of anteiso ester is also comparable to unsaturated jojoba esters, however unsaturated esters are prone to oxidative stability issues, whereas esters derived from branched hydrophobes are not susceptible to such a reaction (see paragraph [0003] of US2004/0076654A1).

Virgin Brown Hair, Ease of Dry Combing—Tips of Hair

| Sample | Formula | Mean Score | 95% LSD | | |
|---|---|---|---|---|---|
| 8 | Low control | 1.43 | A | | |
| 9 | PDMS (30 micron)[1] | 3.86 | | B | |
| 10 | PDMS (1 micron)[1] | 5.71 | | B | C |
| 11 | C17 Anteiso ester[2] | 6.71 | | | C D |
| 12 | Floraester 20[3] | 6.64 | | | C D |
| 13 | Floraester 60[3] | 7.29 | | | C D |
| 14 | High control | 8.71 | | | D |

KEY:
as for samples 1 to 7.

The conclusions from this comparative experiment (samples 8 to 14) include: Improved tip combing performance with anteiso and jojoba esters—this is important given tips typically exhibit more chemical and mechanical damage and are more hydrophilic than the root and body.

Low Lift Hair, Ease of Dry Combing—Body of Hair

| Sample | Formula | Mean Score | 95% LSD | | | D: Si |
|---|---|---|---|---|---|---|
| 15 | Low control | 1.63 | A | | | 0 |
| 16 | C16 Bio-HSA ester[1] | 4.63 | | B | | — |
| 17 | Oleyl erucate[2] | 4.50 | | B | | — |
| 18 | PDMS (1 micron)[3] | 6.50 | | | C | 65 |
| 19 | Floraester 70[4] | 6.38 | | | C | — |
| 20 | Floraester 60[4] | 7.25 | | | C | — |
| 21 | C17 Anteiso ester[5] | 7.50 | | | C D | — |
| 22 | High control | 9.13 | | | | E 56 |

KEY:
[1]= 4,8,12-trimethyl-tridecan-1-ol, stearate;
[2]= 1.0% Tegosoft OER (from Evonik);
[3]= 1% 330,000 cSt Polydimethylsiloxane (from Momentive);
[4]= 1% Jojoba esters (from Floratech);
[5]= 1% 14-Methylhexadecylstearate;
D: Si = deposition of silicone in ppm.

The conclusions from the comparative experiment (samples 15 to 22) include: Near-terminal branched esters deposit effectively on damaged hair (in addition to virgin brown hair), providing comparable dry combing performance to small particle silicones and improved performance versus large particle silicones (large particle silicones typically don't deposit on chemically damaged hair [i.e. "lifted" hair], either via filtration or coacervation).

Low Lift Hair, Ease of Dry Combing—Tips of Hair

| Sample | | Mean Score | 95% LSD | | | |
|---|---|---|---|---|---|---|
| 23 | Low control | 1.38 | A | | | |
| 24 | C16 Bio-HSA ester[1] | 3.50 | | B | | |
| 25 | Oleyl erucate[2] | 3.75 | A | B | | |
| 26 | PDMS (1 micron)[3] | 4.88 | | B | C | |
| 27 | Floraester 70[4] | 6.63 | | | C | D |
| 28 | Floraester 60[4] | 6.94 | | | | D |
| 29 | C17 Anteiso ester[5] | 7.13 | | | | D |
| 30 | High control | 8.88 | | | | E |

KEY:
as for samples to 15 to 22.

The conclusions from the comparative experiment (samples 23 to 30) include: Effective deposition on hair tips is usually the most difficult due to highest degree of damage—these data show that near-terminal branched compounds are more effective than small particle silicone at providing consumer noticeable benefits on tips, which is believed to be due to higher deposition on hair of the near-terminal branched compound.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. A personal care composition comprising:
   (a) a near-terminal branched compound;
   (b) a cosmetically acceptable aqueous carrier;
   wherein the near-terminal branched compound is not present in a gel network; and
   wherein the near-terminal branched compound is a wax ester selected from the group consisting of: 13-methylhexadecylpalmitate, 15-methylhexadecylstearate, 14-methylhexadecyl stearate; 14-methylhexadecyl palmitate; 16-methyloctadecyl stearate; 16-methyloctadecyl palmitate; 12-methyltetradecyl stearate; 12-methyltetradecylpalmitate; 18-methyleicosyl stearate; 18-methyleicosyl palmitate; 13-methylhexadecyl stearate; 15-methylhexadecyl palmitate; 13-methyltetradecyl stearate; 14-methylhexadecanoic acid, tetradecyl ester; 14-methylhexadecanoic acid, hexadecyl ester; 14-methylhexadecanoic acid, octadecyl ester; 16-methyloctadecanoic acid, hexadecyl ester; 18-methyleicosanoic acid, hexadecyl ester; 18-methyleicosanoic acid, tetradecyl ester; 13-methylhexadecyl palmitate, 13-methylhexadecyl stearate; 15-methylhexadecanoic acid, tetradecyl ester; 15-methylhexadecanoic acid, hexadecyl ester; 17-methyloctadecanoic acid, hexadecyl ester, and mixtures thereof.

2. The composition according to claim 1, wherein the near-terminal branched compound as defined in claim 1(a) is at least two different near-terminal branched compounds and wherein neither said near-terminal branched compound is present in a gel network.

3. A conditioning shampoo formulation for cleansing hair comprising:
(a) a near-terminal branched compound according to claim 1(a);
(b) a cosmetically acceptable aqueous carrier;
(c) a cationic polymer;
(d) anionic surfactant;
wherein the near-terminal branched compound is not present in a gel network.

4. The formulation according to claim 3, wherein the formulation comprises about 1 wt % or less of a silicone compound.

5. The formulation according to claim 3, wherein the formulation comprises about 0.5 wt % or less of a silicone compound.

6. The formulation according to claim 4, wherein the silicone compound is a conditioning silicone compound selected from the group consisting of: polydimethylsiloxanes, dimethiconols, aminosilicones, and mixtures thereof.

7. The formulation according to claim 3, wherein the cationic polymer is selected from the group consisting of: polyquaternium-10; a cationic guar; a cationic acrylamide; polyquaternium-76; polyquaternium-6, and mixtures thereof.

8. The formulation according to claim 3, further comprising a dispersed gel network phase comprising either: linear fatty alcohols and an anionic surfactant, or linear fatty alcohols and a cationic surfactant.

9. The formulation according to claim 3, further comprising an anti-dandruff active, wherein the anti-dandruff active is from about 0.01 wt % to about 5 wt %, by total weight of the formulation.

10. The formulation according to claim 3, further comprising a co-surfactant selected from the group consisting of CAPB (cocoamidopropyl betaine), Cocobetaine (CocoB), sodium lauroylamphoacetate (NaLAA), laurylhydroxysultaine (LHS), cocomonoethanol amide (CMEA), and mixtures thereof.

11. A rinse-off conditioner formulation comprising:
(a) a near-terminal branched compound according to claim 1(a);
(b) a cosmetically acceptable aqueous carrier;
(c) a gel network;
wherein the near-terminal branched compound is not present in the gel network.

12. The rinse-off conditioner formulation according to claim 11, wherein the gel network comprises a linear fatty alcohol and a quaternary ammonium compound.

13. The rinse-off conditioner formulation according to claim 11, wherein the formulation comprises up to about 10% of a gel network, by total weight of the formulation.

14. Method of conditioning hair comprising applying the personal care composition according to claim 1 onto hair.

* * * * *